United States Patent
Santi et al.

(10) Patent No.: US 7,259,156 B2
(45) Date of Patent: Aug. 21, 2007

(54) GELDANAMYCIN COMPOUNDS AND METHOD OF USE

(75) Inventors: Daniel V. Santi, San Francisco, CA (US); Zong-Qiang Tian, Fremont, CA (US); Yaoquan Liu, Castro Valley, CA (US); Zhan Wang, El Dorado Hills, CA (US)

(73) Assignee: Kosan Biosciences Incorporated, Hayward, CA (US)

( * ) Notice: Subject to any disclaimer, the term of this patent is extended or adjusted under 35 U.S.C. 154(b) by 270 days.

(21) Appl. No.: 11/133,880

(22) Filed: May 17, 2005

(65) Prior Publication Data

US 2005/0267046 A1 Dec. 1, 2005

Related U.S. Application Data

(60) Provisional application No. 60/573,306, filed on May 20, 2004, provisional application No. 60/584,515, filed on Jun. 30, 2004.

(51) Int. Cl.
*C07D 225/06* (2006.01)
*A61K 31/395* (2006.01)

(52) U.S. Cl. ...................... 514/183; 540/461
(58) Field of Classification Search ............... 540/461; 514/183
See application file for complete search history.

(56) References Cited

U.S. PATENT DOCUMENTS

| | | | |
|---|---|---|---|
| 4,261,989 A | 4/1981 | Sasaki et al. | |
| 5,510,118 A | 4/1996 | Bosch et al. | |
| 5,534,270 A | 7/1996 | De Castro | |
| 5,662,883 A | 9/1997 | Bagchi et al. | |
| 5,932,566 A | 8/1999 | Schnur et al. | |
| 6,015,659 A | 1/2000 | Welch et al. | |
| 6,174,875 B1 | 1/2001 | DeFranco et al. | |
| 6,670,348 B1 | 12/2003 | Rosen et al. | |
| 6,855,705 B1 | 2/2005 | Tian et al. | |
| 6,870,049 B1 | 3/2005 | Tian et al. | |
| 6,875,863 B1 | 4/2005 | Tian et al. | |
| 6,887,993 B1 | 5/2005 | Tian et al. | |
| 2002/0045570 A1 | 4/2002 | Rosen et al. | |
| 2002/0077279 A1 | 6/2002 | Kumar et al. | |
| 2003/0114450 A1 | 6/2003 | Santi et al. | |
| 2004/0053909 A1 | 3/2004 | Snader et al. | |
| 2005/0026894 A1 | 2/2005 | Tian et al. | |

FOREIGN PATENT DOCUMENTS

| | | | |
|---|---|---|---|
| JP | 55-111419 A | 8/1980 | |
| JP | 55-111470 A | 8/1980 | |
| JP | 63-218620 A | 9/1988 | |
| JP | 04-046120 A | 2/1992 | |
| JP | WO94/08578 A2 | 4/1994 | |
| WO | WO 00/03737 A2 | 1/2000 | |
| WO | WO 02/36574 A1 | 5/2002 | |
| WO | WO 02/079167 A1 | 10/2002 | |
| WO | WO 03/066005 A2 | 8/2003 | |

OTHER PUBLICATIONS

An et al., *Cancer Chemother. Pharmacol.* 1997, 40, 60-64, "Depletion of p185$^{erbB2}$, Raf-1 and mutant p53 proteins by geldanamycin derivatives correlates with antiproliferative activity."

Carreras et al., *Anal. Biochem.* 2003, 317, 40-46, "Filter binding assay for the geldanamycin-heat shock protein interaction".

Cheng et al., *J. Med. Chem.* 2005, 48, 645-652, "Synthesis and Enzyme-Specific Activation of Carbohydrate-Geldanamycin Conjugates with Potent Anticancer Activity".

Clevenger et al., *J. Org. Chem.* 69, 4375-4380 (2004), "Biotinylated Geldanamycin".

Eustace et al., *Nature Cell Biology*, 6 (6), 507-514 (2004, web-published May 16, 2004), "Functional proteomic screens reveal an essential extracellular role for hsp90α in cancer cell invasiveness".

Ferrarini et al., *Int. J. Cancer*, 1992, 613-619, "Unusual expression and localization of heat-shock proteins in human tumor cells" (abstract).

Hegmans et al., *Am. J. Pathol.*, 164 (5), 1807-15 (2004), "Proteomic Analysis of Exosomes Secreted by Human Mesothelioma Cells" (abstract).

Hickey et al., *Mol. Cell Biol.* 1989, 9, 2615-2626, "Sequence and Regulations of a Gene Encoding a Human 89-Kilodalton Heat Shock Protein".

(Continued)

*Primary Examiner*—Bruck Kifle
(74) *Attorney, Agent, or Firm*—Yuan Chao

(57) ABSTRACT

Geldanamycin compounds having a structure according to formula I

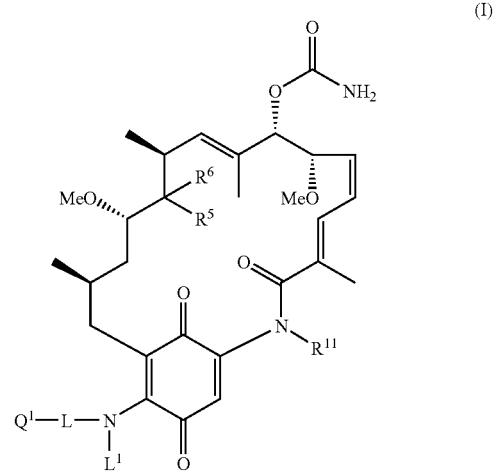

where $Q^1$, L, $L^1$, $R^5$, $R^6$, and $R^{11}$ are as defined herein, are useful for treating a disease or disorder ameliorated by inhibiting the function of extracellular heat shock protein-90.

13 Claims, No Drawings

OTHER PUBLICATIONS

Jez et al., *Chemistry & Biology*, 10, 361-368 (2003), "Crystal Structure and Molecular Modeling of 17-DMAG in Complex with Human HSP90".

López-Ortín et al., *Nature Rev. Mol. Cell Biol.*, 3, 509-519 (2002), "Protease Degradonomics: a New Challenge for Proteomics".

Omura et al., *J. Antibiotics* 1984, 37 (10), 1264-1267, Chemical Modification and Antitumor Activity of Herbimycin A, 8-9-Epoxide, 7-9-Cyclic Carbamate, and 17- or 19-Amino Derivatives.

Pratt, *J. Biol. Chem.*, 268 (29), 21455-21458 (1993), "The Role of Heat Shock Proteins in Regulating the Function, Folding, and Trafficking of the Glucocorticoid Receptor*".

Schnur et al., *J. Med. Chem.*, 38, 3806-3812 (1995), "Inhibition of the Oncogene Product p185$^{erbB-2}$ in Vitro and in Vivo by Geldanamycin and Dihydrogeldanamycin Derivatives".

Schnur et al., *J. Med. Chem.*, 38, 3813-3820 (1995), "erbB-2 Oncogene Inhibition by Geldanamycin Derivatives: Synthesis, Mechanism of Action, and Structure-Activity Relationships".

Sreedhar et al., *FEBS Letters* 562 (1-3), 11-15 (2004), "HSP90 Isoforms: functions, expression and clinical importance".

Tian et al., *Bioorg. Med. Chem.*, 2004, 12, 5317-5329, "Synthesis and Biological Activities of Novel 17-Amino-geldanamycin Derivatives".

Xu et al., *Proc. Natl. Acad. Sci (USA)*, 90, 7074-7078 (1993), "Heat-shock protein hsp90 governs the activity of pp60$^{v-src}$ kinase".

Xu et al., *Proc. Natl. Acad. Sci. (USA)*, 96, 109-114 1999), "Maturation of the tyrosine kinase c-src as a kinase and as a substrate depends on the molecular chaperone Hsp90".

GELDANAMYCIN COMPOUNDS AND METHOD OF USE

CROSS-REFERENCE TO RELATED APPLICATIONS

This application claims the benefit under 35 U.S.C. §119(e) of U.S. Provisional Applications Nos. 60/573,306, filed May 20, 2004, and 60/584,515, filed Jun. 30, 2004; the disclosures of which are incorporated herein by reference.

BACKGROUND OF THE INVENTION

1. Field of the Invention

This invention relates to geldanamycin compounds and methods for their preparation and use, in particular where extracellular heat shock protein 90 is inhibited.

2. Description of Related Art

Geldanamycin belongs to the ansamycin family of natural products, whose members are characterized by a benzenoid nucleus (typically a benzoquinone or hydroquinone nucleus) connected at two meta positions to form a macrocyclic lactam. Besides geldanamycin, the ansamycins include the macbecins, the herbimycins, the TAN-420s, and reblastatin.

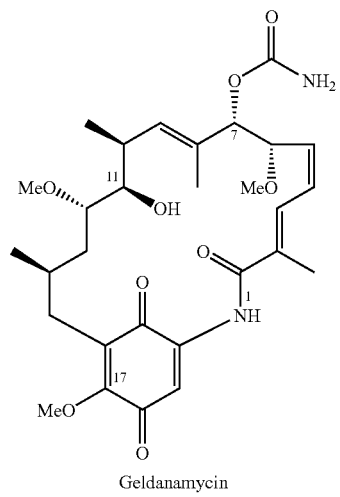

Geldanamycin

Geldanamycin and its derivatives are the most extensively studied of the ansamycins. Although geldanamycin was originally identified as a result of screening for antibiotic activity, current interest in it is based primarily on its cytotoxicity towards tumor cells and, therefore, its potential as an anticancer agent. It is an inhibitor of heat shock protein-90 ("Hsp90"), a chaperone protein that is involved in the folding, activation and assembly of a wide range of proteins ("client proteins"), including key proteins involved in signal transduction, cell cycle control and transcriptional regulation. (Hsp90 exists in a number of isoforms, with the α-isoform being the most common one. For a review on Hsp90 isoforms, see Sreedhar et al., *FEBS Letters* 562 (1-3), 11-15 (2004). Herein, where reference to a specific isoform is intended, abbreviations such as "Hsp90α" or "Hsp90β" will be used, with "Hsp90" reserved for Hsp90 generically.) The binding of geldanamycin to Hsp90 disrupts Hsp90-client protein interactions, preventing the client proteins from folding correctly and rendering them susceptible to proteasome-mediated destruction. Among the Hsp90 client proteins are many mutated or overexpressed proteins implicated in cancer: p53, Bcr-Abl kinase, Raf-1 kinase, Akt kinase, Npm-Alk kinase p185$^{ErB2}$ transmembrane kinase, Cdk4, Cdk6, Wee1 (a cell cycle-dependent kinase), HER2Neu (ErbB2), and hypoxia inducible factor-1α (HIF-1α). However, the hepatotoxicity and poor bioavailability of geldanamycin have lead to its discontinuation as a clinical candidate.

Nevertheless, interest persists in the development of geldanamycin derivatives or analogs (collectively "geldanamycin compounds") having geldanamycin-like bioactivity, but with a better overall spectrum of properties. Position 17 of geldanamycin has been an attractive focal point, chemically speaking, for the synthesis of geldanamycin compounds because its methoxy group is readily displaced by a nucleophile, providing a convenient entry into 17-substituted-17-demethoxygeldanamycin compounds. Further, structure-activity relationship (SAR) studies have shown that structurally and sterically diverse 17-substituents can be introduced without destroying their ability to bind Hsp90. For exemplary disclosures relating to 17-substituted geldanamycin compounds, see Sasaki et al., U.S. Pat. No. 4,261,989 (1981); Schnur et al., U.S. Pat. No. 5,932,566 (1999); Schnur et al., *J. Med. Chem.*, 38, 3806-3812 (1995); Schnur et al., *J. Med. Chem.*, 38, 3813-3820 (1995); Ho et al., WO 00/03737 A2 (2000); Santi et al., US 2003/0114450 A1 (2003); Zhang et al., WO 03/066005 A2 (2003); and Clevenger et al., *J. Org. Chem.* 69, 4375-4380 (2004); the disclosures of which are incorporated by reference. The SAR inferences are supported by the X-ray crystal co-structure of the complex between Hsp90α and a geldanamycin derivative (17-DMAG, v. infra), showing that the 17-substituent projects out from the binding pocket and into the solvent (Jez et al., *Chemistry & Biology*, 10, 361-368 (2003)).

The best-known 17-substituted geldanamycin is 17-allylamino-17-demethoxygeldanamycin ("17-AAG"), currently undergoing clinical trials. Another noteworthy 17-substituted geldanamycin is 17-(2-dimethylaminoethyl)amino-17-demethoxygeldanamycin ("17-DMAG"), also undergoing clinical trials (Snader et al., WO 02/079167 A1 (2002), incorporated by reference). Like geldanamycin, both 17-AAG and 17-DMAG must be administered with care due to their cytotoxicity.

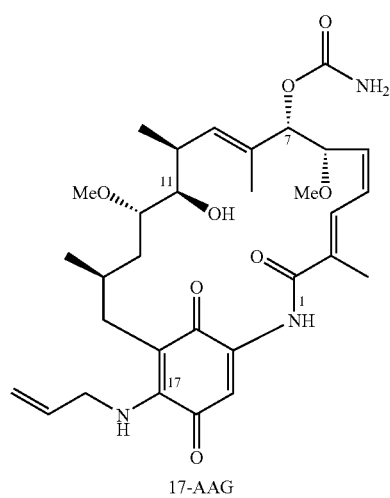

17-AAG

-continued

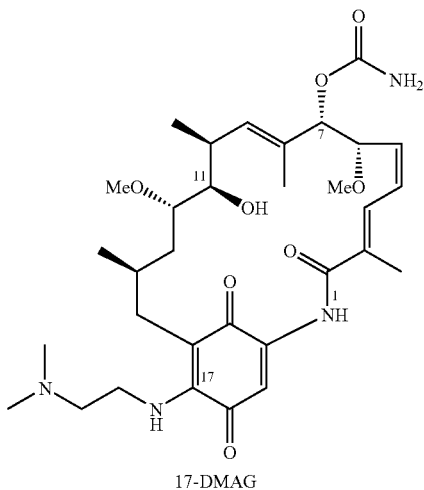

17-DMAG

While most studies concerning the function of Hsp90 have focused on its activity inside cells, there have been a few reports on the extracellular occurrence of Hsp90, usually in association with cancer cells. Eustace et al., *Nature Cell Biology*, 6 (6), 507-514 (2004, web-published 16 May 2004) ("Eustace et al."), reported that Hsp90α plays an essential extracellular role in cancer cell invasiveness. They found that fibrosarcoma and breast cancer cells express Hsp90α extracellularly, where it interacts with matrix metalloproteinase-2 ("MMP-2") and that inhibition of extracellular Hsp90α by geldanamycin decreases both MMP-2 activity and cancer cell invasiveness. Their hypothesis is that matrix metalloproteinases ("MMPs") are responsible for the degradation of the extracellular matrix, thereby facilitating the invasive action of cancer cells, and that Hsp90α plays a chaperone protein role in the activation of MMPs. Other reported occurrences of extracellular Hsp90 include: Hegmans et al., *Am. J. Pathol.*, 164 (5), 1807-15 (2004); Xu et al., *Proc. Natl. Acad. Sci. (USA)*, 96, 109-114 1999); Xu et al., *Proc. Natl. Acad. Sci (USA)*, 90 7074-7078 (1993); Ferrarini et al., *Int. J. Cancer*, 1992, 613-619; and Pratt, *J. Biol. Chem.*, 268 (29), 21455-21458 (1993).

A drawback to using Hsp90 inhibitors such as geldanamycin, 17-AAG, and 17-DMAG in therapies targeting intracellular Hsp90 is their cytotoxicity, with concomitant lowered therapeutic indices. However, for therapies in which the target is extracellular Hsp90, one can theoretically use Hsp90 inhibitors that do not cross cell membranes and enter cells. If such compounds are still able to bind to and inhibit extracellular Hsp90, their cell impermeability should lead to reduced cytotoxicities and higher therapeutic indices.

BRIEF SUMMARY OF THE INVENTION

In one aspect, this invention provides a method for treating a disease or disorder ameliorated by inhibiting the function of extracellular Hsp90, comprising administering to a subject afflicted with such disease or disorder, in an amount sufficient to inhibit the function of extracellular Hsp90, a compound having an $IC_{50}$ towards SkBr3 cells of 1,000 nM or greater and a $K_d$ for binding to Hsp90α of 2 μM or less.

In another aspect, this invention provides a method for treating a disease or disorder ameliorated by inhibiting the function of extracellular Hsp90, comprising administering to a subject afflicted with such disease or disorder, in an amount sufficient to inhibit the function of extracellular Hsp90, a compound having a structure according to formula (I):

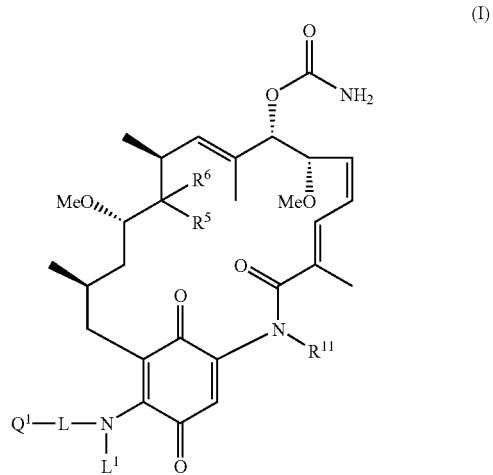

(I)

and the pharmaceutically acceptable solvates, hydrates, salts, and prodrug forms thereof, wherein $Q^1$ is a tertiary amine N-oxide group, a quaternary nitrogen group, a sulfonic acid group, a phosphonic acid group, a zwitterionic group, a carboxylic acid group, a glycoside group, or a biotinyl group;

L is a linker moiety separating $Q^1$ and the NH group by between 2 and 12 atoms, with the proviso that L can be absent if $Q^1$ is a glycoside group;

$L^1$ is H or forms in combination with L and the nitrogen to which they are commonly bonded a 3, 4, 5, 6, or 7 membered nitrogen-containing heterocyclic ring structure;

$R^5$ is H, $OR^8$, halogen, $OC(=O)R^8$, $O(C=O)N(R^8R^9)$, $OSO_2R^{10}$, or $O(C=O)NHSO_2N(R^8R^9)$;

$R^6$ is H or halogen; or $R^5$ and $R^6$ combine to form $=O$ or $=NOR^8$;

each $R^8$ is independently H, $C_1$-$C_5$ alkyl, $C_2$-$C_5$ alkenyl, $C_2$-$C_5$ alkynyl, or $C_3$-$C_6$ cycloalkyl;

each $R^9$ is independently H, $C_1$-$C_5$ alkyl, $C_2$-$C_5$ alkenyl, $C_2$-$C_5$ alkynyl, or $C_3$-$C_6$ cycloalkyl;

or $R^8$ and $R^9$ form, in combination with a nitrogen atom to which they are commonly attached, a substituted or unsubstituted 3, 4, 5, or 6 membered heterocyclic ring;

$R^{10}$ is $C_1$-$C_5$ alkyl, $C_2$-$C_5$ alkenyl, $C_2$-$C_5$ alkynyl, or $C_3$-$C_6$ cycloalkyl; and $R^{11}$ is H, $C_1$-$C_5$ alkyl, $C_2$-$C_5$ alkenyl, $C_2$-$C_5$ alkynyl.

In another aspect of this invention, there is provided a compound having a structure according to formula (II)

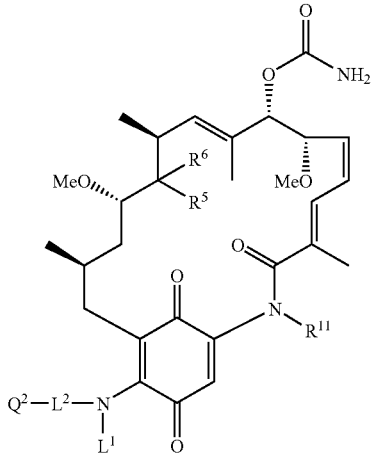

(II)

and the pharmaceutically acceptable solvates, hydrates, salts, and prodrug forms thereof, wherein
$Q^2$ is a tertiary amine N-oxide group; and
$L^2$ is a linker moiety separating $Q^2$ and the NH group by between 2 and 12 atoms; and
$L^1$, $R^5$, $R^6$, and $R^{11}$ are as defined above.

In another aspect of this invention, there is provided a compound having a structure according to formula (III)

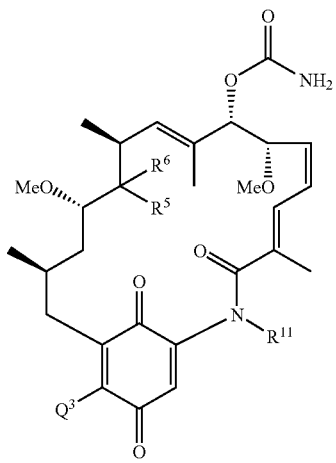

(III)

and the pharmaceutically acceptable solvates, hydrates, salts, and prodrug forms thereof, wherein
$Q^3$ is selected from the group consisting of

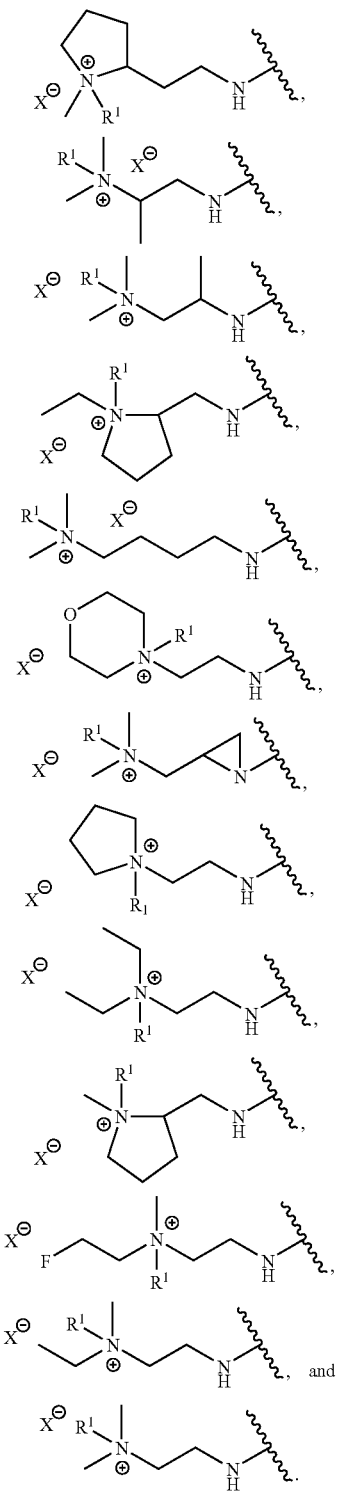

-continued $R^1$ is $C_1$-$C_5$ alkyl, $C_1$-$C_5$ alkenyl, $C_1$-$C_5$ alkyl, $CH_2CN$, or $CH_2CONH_2$;
$R^5$, $R^6$, and $R^{11}$ are as defined above; and
$X^\ominus$ is a pharmaceutically acceptable counteranion.

In another aspect of the invention, there is provided a compound having a structure according to formula IV:

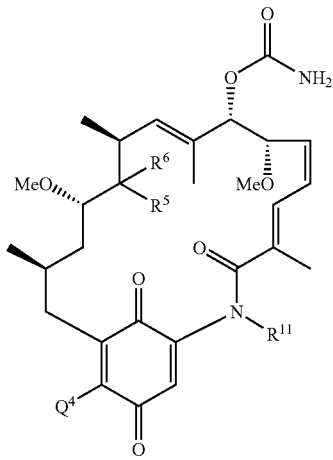

(IV)

and the pharmaceutically acceptable solvates, hydrates, salts, and prodrug forms thereof, wherein
$Q^4$ is selected from the group consisting of

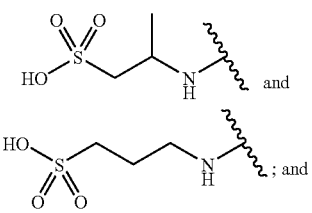

$R^5$, $R^6$, and $R^{11}$ are as defined above.

In another aspect of this invention, there is provided a compound having a structure according to formula V

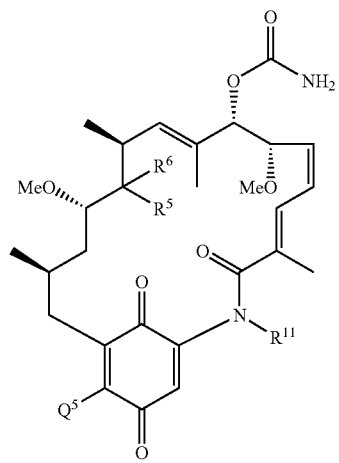

(V)

and the pharmaceutically acceptable solvates, hydrates, salts, and prodrug forms thereof, wherein $Q^5$ is selected from the group consisting of

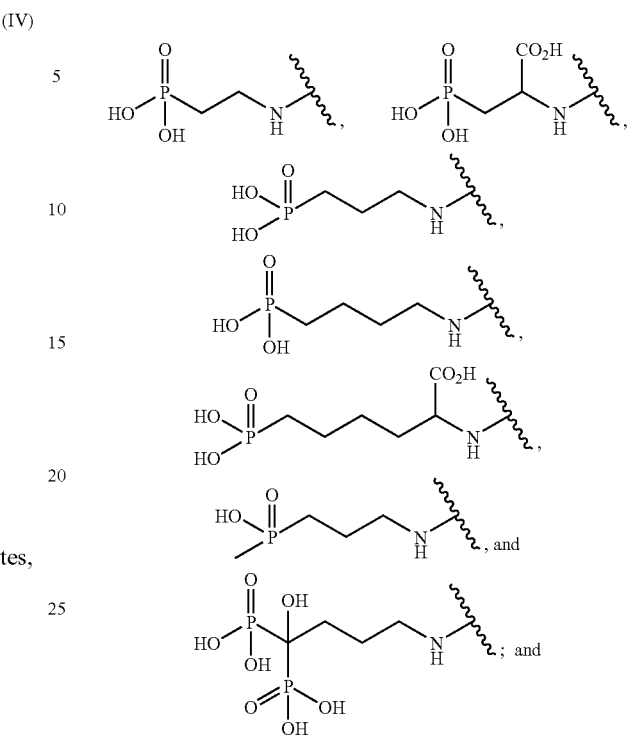

$R^5$, $R^6$, and $R^{11}$ are as defined above.

In another aspect of the invention, there is provided a compound having a structure according to formula VI

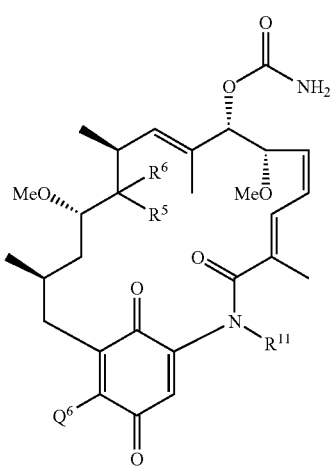

(VI)

and the pharmaceutically acceptable solvates, hydrates, salts, and prodrug forms thereof, wherein
$Q^6$ is selected from the group consisting of

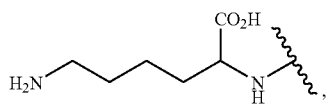

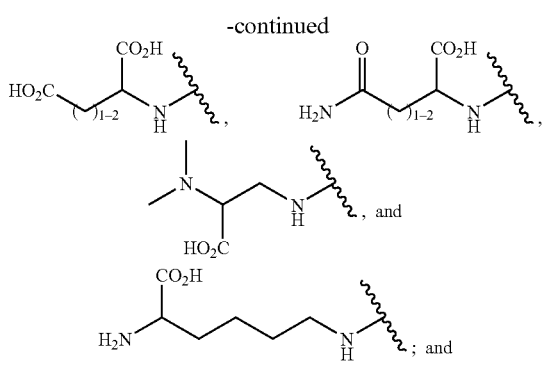

$R^5$, $R^6$, and $R^{11}$ are as defined above.

In another aspect of the invention, there is provided a method for identifying, from a library of compounds, candidate compounds for use in a treatment for a disease or disorder ameliorated by inhibiting the function of extracellular Hsp90, comprising the steps of:

(a) determining the $IC_{50}$ of the compounds in the library towards SkBr3 cells;

(b) determining the dissociation constant $K_d$ for the binding to Hsp90α of the compounds in the library; and (c) selecting as candidate compounds those compounds in the library having an $IC_{50}$ of 1,000 nM or greater and a $K_d$ of 2 μM or less.

In another aspect of the invention, there is provided a pharmaceutical formulation comprising a compound of this invention and an excipient.

In aspect of the invention embodiment, there is provided the use of a compound of this invention for the preparation of a medicament for the treatment of a disease or disorder ameliorated by inhibiting the function of extracellular Hsp90.

DETAILED DESCRIPTION OF THE INVENTION

Definitions

"Alkyl" means an optionally substituted straight or branched chain hydrocarbon moiety having the specified number of carbon atoms in the chain (e.g., as in "$C_1$-$C_8$ alkyl") or, where the number of carbon atoms is not specified, up to 5 carbon atoms in the chain.

"Alkenyl" means an optionally substituted straight or branched chain hydrocarbon moiety having at least one carbon-carbon double bond and the specified number of carbon atoms in the chain (e.g., as in "$C_2$-$C_8$ alkenyl") or, where the number of carbon atoms is not specified, up to 5 carbon atoms in the chain.

"Alkynyl" means an optionally substituted straight or branched chain hydrocarbon moiety having at least one carbon-carbon triple bond and the specified number of carbon atoms in the chain (e.g., as in "$C_2$-$C_8$ alkynyl") or, where the number of carbon atoms is not specified, up to 5 carbon atoms in the chain.

"Alkylaryl," "arylalkyl," "heterocycloalkyl," "alkylheteroaryl," "alkylheterocycle" and the like mean an aryl, heterocyclic, or heteroaryl group, as the case may be, bonded directly to an alkyl moiety, as in benzyl, phenethyl, and the like.

"Aryl" means a monocyclic or bicyclic aromatic hydrocarbon ring system having 6 to 12 carbon atoms in the ring portion, such as phenyl, napthyl, and biphenyl moieties, each of which is optionally substituted at one or more positions.

"Cycloalkyl" means an optionally substituted, saturated cyclic hydrocarbon ring system, preferably containing 1 to 3 rings and 3 to 7 carbons per ring (unless a different number of carbons is indicated), which may be further fused with an unsaturated $C_3$-$C_7$ carbocyclic ring. Exemplary cycloalkyl ring systems include cyclopropyl, cyclobutyl, cyclopentyl, cyclohexyl, cycloheptyl, cyclooctyl, cyclodecyl, cyclododecyl, and adamantyl.

"Halogen" or "halo" means fluorine, chlorine, bromine and iodine.

"Heterocycle", "heterocyclic," or "heterocyclo" means an optionally substituted, fully saturated or unsaturated, aromatic or nonaromatic ring system, for example a 4 to 7 membered monocyclic, 7 to 11 membered bicyclic, or 10 to 15 membered tricyclic ring system, which has at least one heteroatom in at least one carbon atom-containing ring. "Heteroaryl" means a heterocycle in which the ring system is aryl. Each ring of the hetero-cyclic group containing a heteroatom may have 1, 2 or 3 heteroatoms selected from N, O and S, where the N and S optionally may be oxidized and the N optionally may be quaternized.

Exemplary monocyclic heterocyclic ring systems include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridinyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1,1-dioxothienyl, dioxanyl, isothiazolidinyl, thietanyl, thiiranyl, triazinyl, and triazolyl, and the like. Preferred heterocyclo groups include pyridinyl, pyrazinyl, pyrimidinyl, pyrroyl, pyrazolyl, imidazolyl, thiazolyl, oxazolyl, isoxazolyl, thiadiazolyl, oxadiazolyl, thienyl, furanyl, quinolinyl, isoquinolinyl, and the like.

Where it is indicated that a group may be substituted, for example by use "substituted or unsubstituted" or "optionally substituted" phrasing, such group may have one or more independently selected substituents, preferably one to five in number, more preferably one or two in number. It is understood that substituents and substitution patterns can be selected by one of ordinary skill in the art to provide compounds that are chemically stable and that can be synthesized by techniques known in the art as well as the methods set forth herein. Examples of suitable substituents include alkyl, alkenyl, alkynyl, aryl, halo, trifluoromethoxy, trifluoromethyl, hydroxy, alkoxy, cycloalkyloxy, heterocyclooxy, alkanoyl, alkanoyloxy, amino, alkylamino quarternary ammonium, aralkylamino, cycloalkylamino, heterocycloamino, dialkylamino, alkanoylamino, thio, alkylthio, cycloalkylthio, heterocyclothio, ureido, nitro, cyano, carboxy, caroboxyalkyl, carbamyl, alkoxycarbonyl, alkylthiono, arylthiono, alkylsulfonyl, sulfonamindo, aryloxy, and the like, in addition to those specified herein. The substituent may be further substituted, for example, by halo, hydroxy, alkyl, alkoxy, aryl, substituted aryl, substituted alkyl, substituted aralkyl, and the like. Preferably, the substituent(s) for alkyl, alkenyl, and alkynyl moieties are from one to three in number and are independently selected from N-pyrrolidinyl, N-morpholinyl, N-azetidinyl, hydroxyl, halo, alkoxyl, cyano, amino, alkylamino, and dialkylamino. Preferably, the substituent(s) for aryl, cycloalkyl, and heterocycloalkyl moieties are from one to three in number and are independently selected from alkyl, alkenyl, alkynyl, hydroxyalkyl, haloalkyl, hydroxyl, halo, alkoxyl, cyano, aminoalkyl, alkylaminoalkyl, dialkylaminoalkyl, amino, alkylamino, and dialkylamino.

"Pharmaceutically acceptable salt" means a salt of a compound suitable for pharmaceutical formulation. Suitable pharmaceutically acceptable salts include acid addition salts which may, for example, be formed by mixing a solution of a compound with a solution of a pharmaceutically acceptable acid such as hydrochloric acid, hydrobromic acid, sulfuric acid, fumaric acid, maleic acid, succinic acid, benzoic acid, acetic acid, citric acid, tartaric acid, phosphoric acid, carbonic acid, or the like. Where a compound carries one or more acidic moieties, pharmaceutically acceptable salts may be formed by treatment of a solution of the compound with a solution of a pharmaceutically acceptable base, such as lithium hydroxide, sodium hydroxide, potassium hydroxide, tetraalkylammonium hydroxide, lithium carbonate, sodium carbonate, potassium carbonate, ammonia, alkylamines, or the like. Those skilled in the art will appreciate that, in the case of a compound where the group $Q^1$ is an acidic group such as a carboxylic acid, sulfonic acid, or phosphonic acid, such compound is often most conveniently provided as its salt, for example its sodium, potassium or lithium salt.

The present invention includes within its scope prodrugs of the compounds of this invention. Such prodrugs are in general functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to a subject in need thereof. Conventional procedures for the selection and preparation of suitable prodrug derivatives are described, for example, in *Design of Prodrugs*, Bundgaard, ed., Elsevier, 1985. Prodrugs include esters that hydrolyze in vivo (for example in the human body) to produce a compound of this invention or a salt thereof. Suitable ester groups include, without limitation, those derived from pharmaceutically acceptable aliphatic carboxylic acids, particularly alkanoic, alkenoic, cycloalkanoic and alkanedioic acids, in which each alkyl or alkenyl moiety preferably has no more than six carbon atoms. Illustrative esters include formates, acetates, propionates, butyrates, acrylates, citrates, succinates, and ethylsuccinates.

Unless particular stereoisomers are specifically indicated (e.g., by a bolded or dashed bond at a relevant stereocenter in a structural formula, by depiction of a double bond as having E or Z configuration in a structural formula, or by use of stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by the present invention. Polymorphic crystalline forms and solvates and hydrates are also encompassed within the scope of this invention.

Those skilled in the art will appreciate that compounds may have tautomeric forms (e.g., keto and enol forms), resonance forms, and zwitterionic forms that are equivalent to those depicted in the structural formulae used herein and that the structural formulae encompass such tautomeric, resonance, or zwitterionic forms.

Where a range is stated, as in "$C_1$ to $C_5$ alkyl" or "5 to 10%," such range includes the end points of the range.

Compounds and Methods

The disease or disorder treatable using the compounds and methods of this invention is one ameliorated by inhibiting the function of extracellular Hsp90 in a subject afflicted with such disease or disorder. In most instances the ultimate molecular target is not Hsp90 itself, but, rather, one or more client proteins for which Hsp90 performs an essential chaperone function, assisting its folding into the conformation required for biological activity. If the functioning of the extracellular Hsp90 is inhibited, the client protein cannot be activated and is eventually destroyed by proteases. The disease or disorder can be cancer, more particularly fibrosarcoma or breast cancer.

A characteristic associated with cancer invasiveness and metastasis is the degradation of the extracellular matrix, thereby facilitating growth of the tumor. Extra-cellular MMP has been implicated in the degradation process, as evidenced by the detection of increased MMP expression in almost all human cancers. López-Ortin et al., *Nature Rev. Mol. Cell Biol.*, 3, 509-519 (2002). Eustace et al., cited supra, have proposed that Hsp90α plays an essential chaperone protein role in the activation of extracellular MMP. Consequently, inhibition of extracellular Hsp90α or other extracellular Hsp90 performing a similar function can lead to diminished MMP activity and, in turn, diminished tumor invasiveness.

The extracellular Hsp90 whose function is inhibited can be one that is secreted in normal amounts by a cell, but whose client protein, however, is overexpressed. Or, alternatively, the extracellular Hsp90 can be itself overexpressed or oversecreted. Or, both the client protein and the Hsp90 are each present in normal amounts, but, in the context of the disease or disorder sought to be treated, inhibition of the Hsp90 and consequently its client protein is desired. In a particular embodiment, the extracellular Hsp90 that is inhibited is Hsp90α.

Preferably, the subject (which can be a human or other mammal) is screened to detect the presence of the extracellular Hsp90 that is to be inhibited. Methodology for the detection of extracellularly expressed Hsp90 is disclosed in Eustace et al., cited supra, and incorporated herein by reference. More preferably, the screening provides a measure of the amount of extracellular Hsp90 secreted, compared to the normal amount for a subject not afflicted with the disease or disorder.

Clinically, an amelioration of a disease or condition treated according to this invention can be manifested in any number of ways, including a reduction in the size or number of the cancerous growth and/or a reduction in associated symptoms. The pathologically relevant response can be the inhibition of cancer cell proliferation, reduction in the size of the cancer or tumor, prevention of further metastasis, and inhibition of tumor angiogenesis.

Preferably, the compounds of this invention have an $IC_{50}$ towards SkBr3 cells of 1,000 nM or greater in combination with a $K_d$ for binding to Hsp90α of 2 μM or less. Hitherto, Hsp90 inhibitors have generally been used to target intracellular Hsp90, for which an ability to enter into a cell is a prerequisite. However, such Hsp90 inhibitors tend to be quite cytotoxic, resulting in low therapeutic indices. In the instant invention, the target is extracellular Hsp90. While not being bound by theory, we believe that compounds according to formula I have a group $Q^1$, which, either because of polarity, size, or other factor, renders them incapable of entering cells; hence, their low cytotoxicity, as manifested by an $IC_{50}$ of 1,000 nM or greater against SkBr3 cells. Yet, at the same time, the fundamental molecular characteristics that enable geldanamycin to bind to and inhibit Hsp90 have been preserved, resulting in their being strong Hsp90 binders, as manifested by a $K_d$ (dissociation constant) for binding to Hsp90α of 2 μM or less. This combination of traits makes them desirable and effective compounds for treatments in which extracellular Hsp90 is the target.

Turning now to formulae I through V, in a preferred embodiment $R^5$ is OH, $R^6$ and $R^{11}$ are each H, corresponding to chemical structures represented by formulae Ia through Va, respectively, with $Q^1$, $Q^2$, $Q^3$, $Q^4$, $Q^5$, L, $L^1$ and $L^2$ retaining the meanings assigned in the BRIEF SUMMARY OF THE INVENTION section.

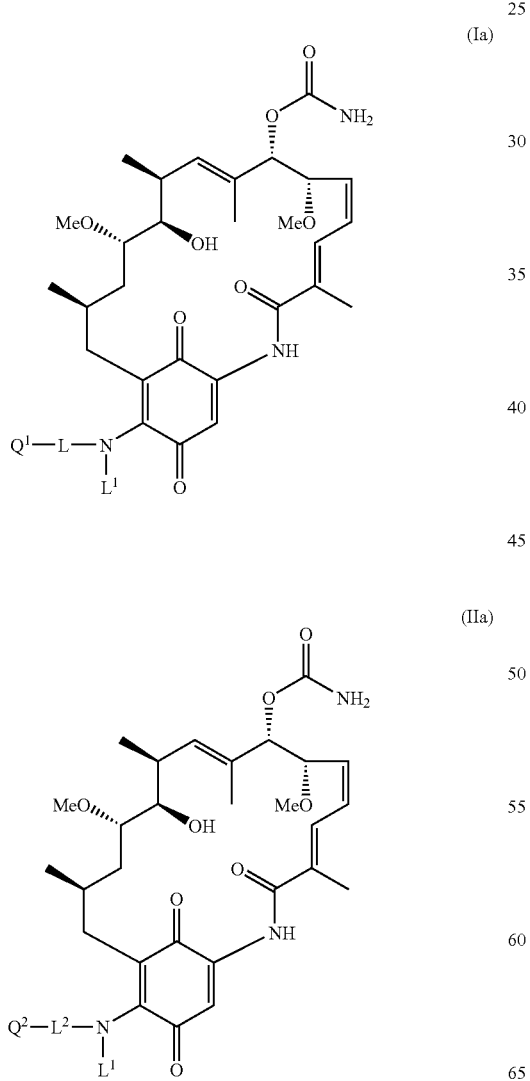

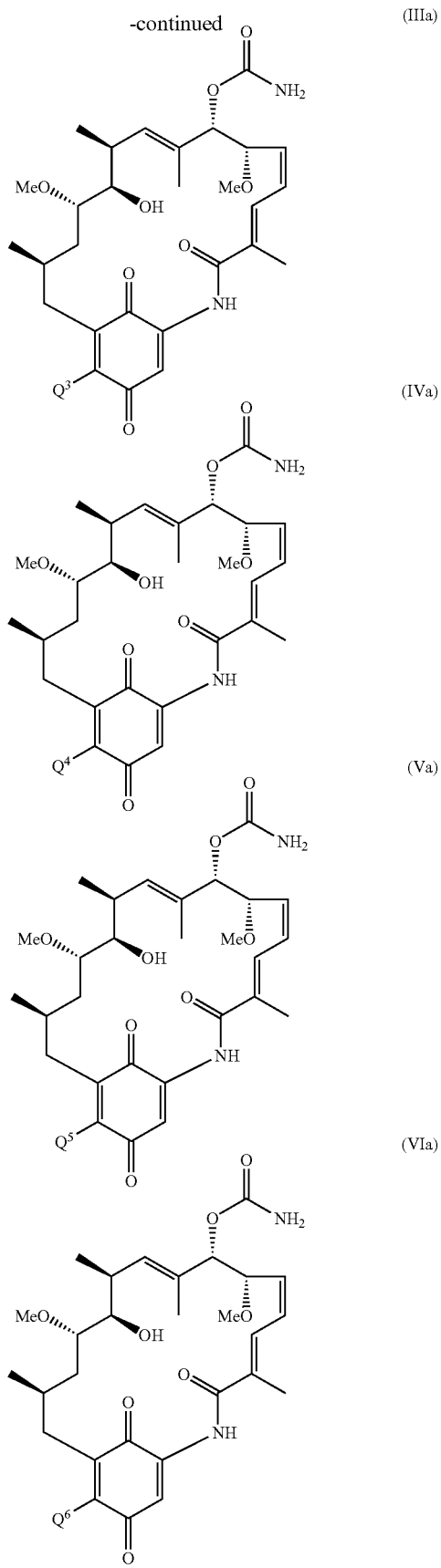

Where L¹ forms in combination with L and the nitrogen to which L¹ and L are commonly bonded a 3, 4, 5, 6, or 7 membered nitrogen containing heterocyclic ring structure, such ring structure preferably is an aziridinyl, azetidinyl, pyrrolidinyl, piperidinyl, or an azepanyl ring structure. More preferably, such ring structure is an aziridinyl, azetidinyl, or pyrrolidinyl ring structure.

Illustrative specific compounds according to this invention include compounds 1 through 10:

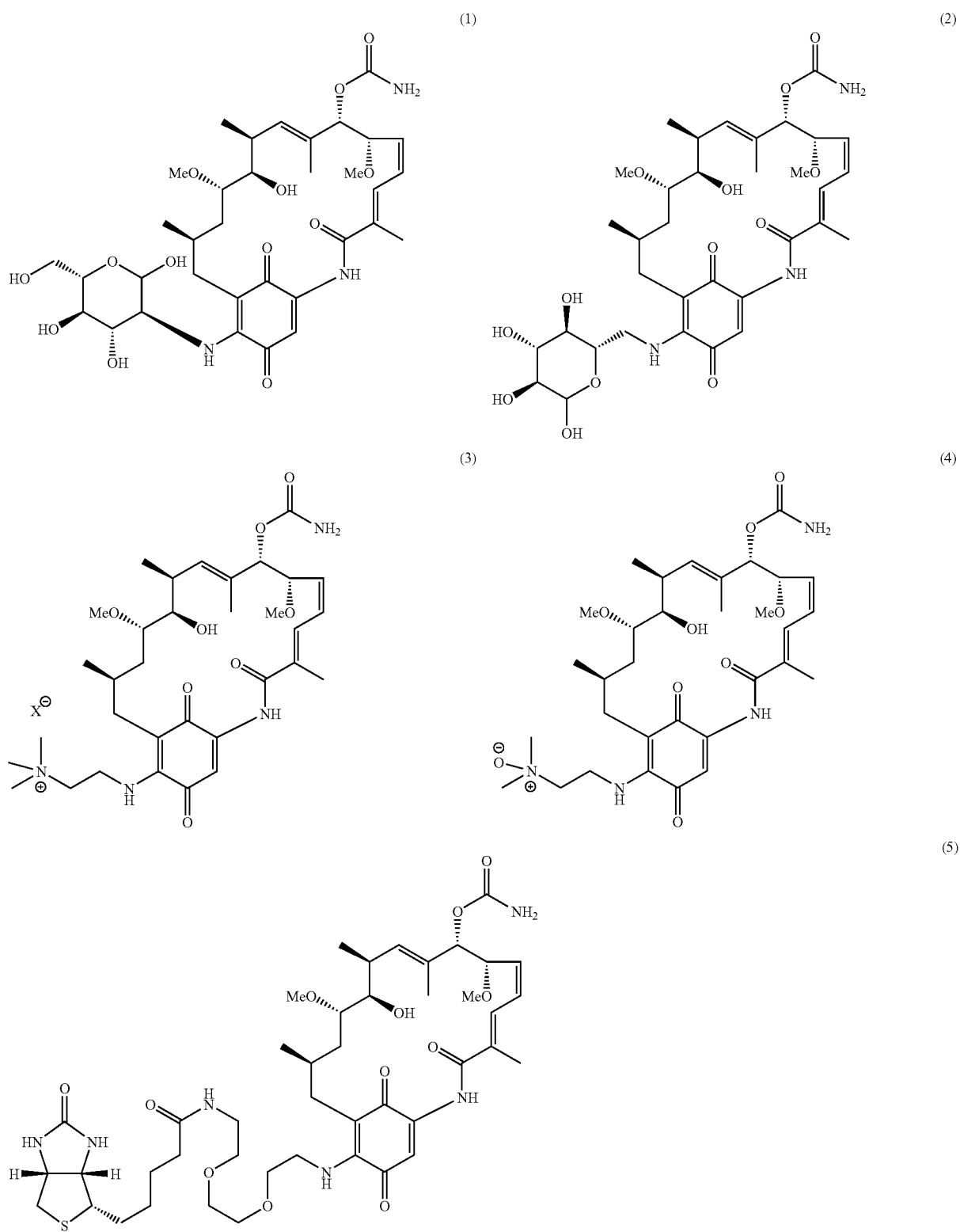

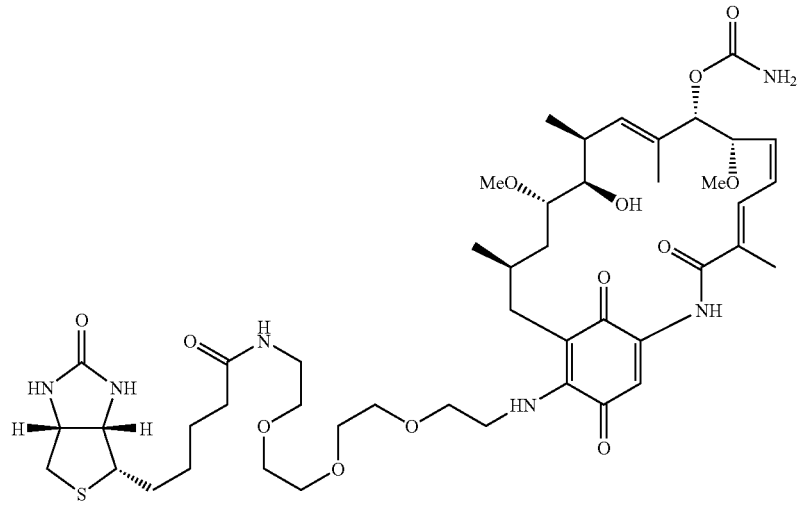

(6)

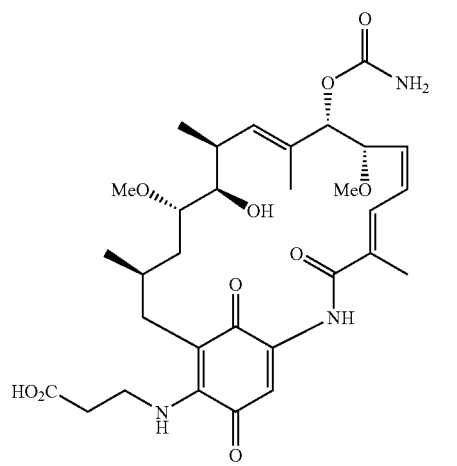

(7)

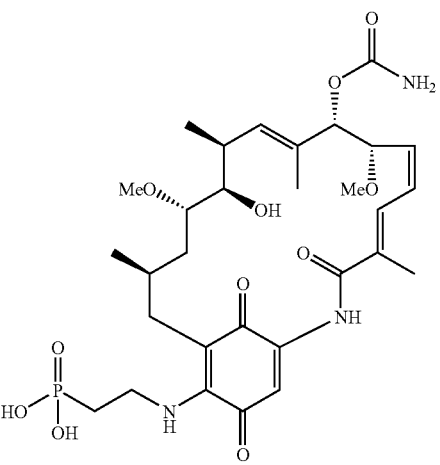

(8)

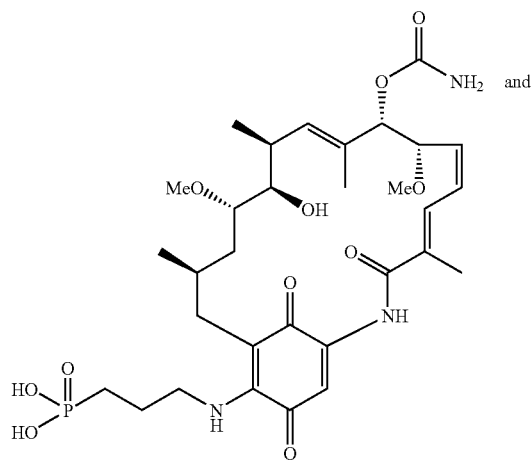

(9)

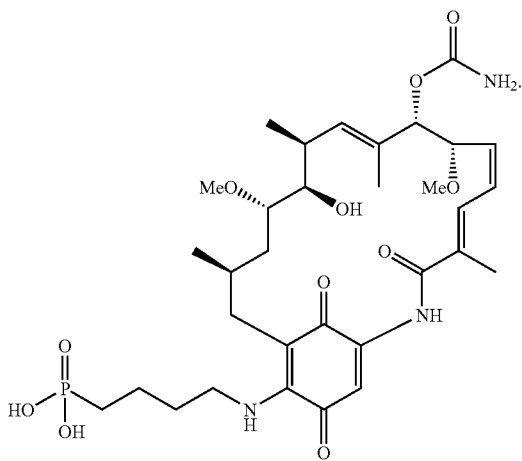

(10)

(In compound 3, $X^\ominus$ is a pharmaceutically acceptable counteranion such as chloride, acetate, citrate, fumarate, maleate, succinate, benzoate, sulfate, tartrate, and the like.)

This invention can be used to screen for drug candidate compounds for use in a method for treating a disease or disorder ameliorated by inhibiting the function of extracellular Hsp90. Desirable drug candidate compounds are those that bind to strongly to Hsp90 (in particular Hsp90α) but yet exhibit low cytotoxicity. Binding strength to Hsp90α can be quantitated in terms of a compound's dissociation constant $K_d$ for binding to Hsp90α, a smaller $K_d$ being indicative of stronger binding. Preferably $K_d$ is 2 µM or less. At the same time a desirable potential lead compound exhibits low cytotoxicity, which can be quantitated by a compound's $IC_{50}$ towards a reference cell line such as SkBr3 cells. Preferably, $IC_{50}$ is 1,000 nM or greater, indicative of relatively low cytotoxicity. Thus, potential lead compounds, or candidate compounds, can be selected from a library of compounds by determining $K_d$ and $IC_{50}$ for each compound and selecting those for which $K_d$ is 2 µM or less and $IC_{50}$ is 1,000 nM or greater. The compounds in the library can be screened one at a time, as each is synthesized. Or, one can collect an entire library or a sub-library and screen such compounds at more or less at the same time. The size of a library can range from a few compounds to hundreds or even thousands of compounds.

Cancers that may be treated by the method of this invention include: cancers of the head and neck which include tumors of the head, neck, nasal cavity, paranasal sinuses, nasopharynx, oral cavity, oropharynx, larynx, hypopharynx, salivary glands, and paragangliomas; cancers of the liver and biliary tree, particularly hepatocellular carcinoma; intestinal cancers, particularly colorectal cancer; treat ovarian cancer; small cell and non-small cell lung cancer; breast cancer sarcomas, such as fibrosarcoma, malignant fibrous histiocytoma, embryonal rhabdomysocarcoma, leiomyosarcoma, neurofibrosarcoma, osteosarcoma, synovial sarcoma, liposarcoma, and alveolar soft part sarcoma; neoplasms of the central nervous systems, particularly brain cancer; lymphomas such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma. The method of treating such diseases comprises administering a therapeutically effective amount of a compound of this to a subject. The method may be repeated as necessary.

Compounds of this invention can be administered in combination with other anti-cancer or cytotoxic agents, including alkylating agents, angiogenesis inhibitors, antimetabolites, DNA cleavers, DNA crosslinkers, DNA intercalators, DNA minor groove binders, enediynes, heat shock protein 90 inhibitors, histone deacetylase inhibitors, microtubule stabilizers, nucleoside (purine or pyrimidine) analogs, nuclear export inhibitors, proteasome inhibitors, topoisomerase (I or II) inhibitors, tyrosine kinase inhibitors. Specific anti-cancer or cytotoxic agents include β-lapachone, ansamitocin P3, auristatin, bicalutamide, bleomycin, bleomycin, bortezomib, busulfan, calicheamycin, callistatin A, camptothecin, capecitabine, CC-1065, cisplatin, cryptophycins, daunorubicin, discodermolide, disorazole, docetaxel, doxorubicin, duocarmycin, dynemycin A, epothilones, etoposide, floxuridine, floxuridine, fludarabine, fluoruracil, gefitinib, geldanamycin, 17-allylamino-17-demethoxygeldanamycin (17-AAG), 17-(2-dimethylaminoethyl)amino 17-demethoxygeldanamycin (17-DMAG), gemcitabine, hydroxyurea, imatinib, interferons, interleukins, irinotecan, leptomycin B, maytansine, methotrexate, mitomycin C, oxaliplatin, paclitaxel, spongistatins, suberoylanilide hydroxamic acid (SAHA), thiotepa, topotecan, trichostatin A, vinblastine, vincristine, and vindesine.

Preferably, compounds of this invention are provided in a purified and isolated form, for example following column chromatography, high-pressure liquid chromatography, recrystallization, or other purification technique. Where particular stereoisomers of compounds of this invention are specified, such stereoisomers preferably are substantially free of other stereoisomers.

Compounds of this invention may be used in a pharmaceutical formulation comprising a compound of this invention and an excipient. Excipients that may be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., *Remington: The Science and Practice of Pharmacy*, 20th Ed. (Lippincott Williams & Wilkins 2003), the disclosure of which is incorporated herein by reference.

The composition may be in any suitable form such as solid, semisolid, or liquid form. In general, the pharmaceutical preparation will contain one or more of the compounds of the invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, pessaries, solutions, emulsions, suspensions, and any other form suitable for use. The carriers that can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid, or liquified form. In addition, auxiliary stabilizing, thickening, and coloring agents and perfumes may be used.

Where applicable, compounds of this invention may be formulated as microcapsules and nanoparticles. General protocols are described for example, in Bosch et al., U.S. Pat. No. 5,510,118 (1996); De Castro, U.S. Pat. No. 5,534,270 (1996); and Bagchi et al., U.S. Pat. No. 5,662,883 (1997), which are all incorporated herein by reference. By increasing the ratio of surface area to volume, these formulations allow for the oral delivery of compounds that would not otherwise be amenable to oral delivery.

Dosage levels of the compounds of the present invention are of the order from about 0.1 mg to about 100 mg per kilogram of body weight per day, preferably from about 1 mg to about 50 mg per kilogram of body weight per day. More preferably, the dosage levels are from about 5 mg to about 20 mg per kilogram of body weight per day, corresponding to 350 mg to 1400 mg per patient per day, assuming a 70 kg patient. The compounds of the present invention may be administered on an intermittent basis, i.e., at semi-weekly, weekly, semi-monthly, or monthly intervals.

The amount of active ingredient that may be combined with the carrier materials to produce a single dosage form will vary depending upon the host treated and the particular mode of administration. For example, a formulation intended for oral administration to humans may contain carrier material, which may vary from about 5 percent to about 95 percent of the total composition. Dosage unit forms will generally contain from about 5 mg to about 500 mg of active ingredient.

It will be understood, however, that the specific dose level for any particular patient will depend on a variety of factors. These factors include the activity of the specific compound employed; the age, body weight, general health, sex, and diet of the subject; the time and route of administration and the rate of excretion of the drug; whether a drug combination is employed in the treatment; and the severity of the particular disease or condition for which therapy is sought.

The practice of this invention can be further understood by reference to the following examples, which are provided by way of illustration and not of limitation.

EXAMPLE 1

Compounds I in which $Q^1$ is a tertiary amine N-oxide (i.e., compounds II) can be synthesized by the reaction of a corresponding geldanamycin compound with a suitable amine followed by oxidation to the N-oxide, as shown by procedure of Scheme 1 using (2-dimethylamino)ethylamine as an exemplar:

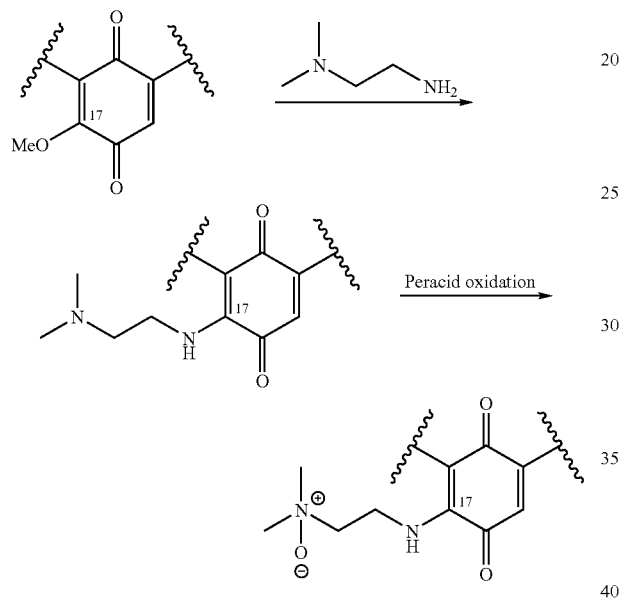

The following detailed procedure used to synthesize compound 4 ([2-(17-demethoxygeldanamycin-17-ylamino)-ethyl]dimethylamine N-oxide) is representative.

17-DMAG was synthesized from geldanamycin as follows: (2-Dimethyl-amino)ethylamine 0.2 mmol) was added to a solution of geldanamycin (56 mg, 0.1 mmol) in 1,2-dichloroethane (4 mL) at 20° C. The mixture was stirred at 20° C. until the geldanamycin was fully consumed as indicated by thin layer chromatography ("TLC"). The crude product was purified either by flash chromatography or by reversed-phase high pressure liquid chromatography ("HPLC"), giving the product 17-DMAG as a purple solid. The preparation of 17-DMAG has also been described in Snader et al., U.S. 2004/0053909 A1 (2004), the disclosure of which is incorporated herein by reference.

To a solution of 17-DMAG in dichloromethane (1 mL) was added 3-chloroperbenzoic acid (77% max, 12 mg, 50 μmol max). The mixture was stirred at 20° C. for 20 h. LC/MS showed that the reaction was complete. The crude product was purified by HPLC on a C18 column, eluted using a gradient of acetonitrile in water. The product compound 4 was obtained as a purple solid, 7 mg. $^{13}$C NMR (CDCl$_3$, 100 MHz) δ (relative to CDCl$_3$ at 77.0 ppm) 12.1, 12.5, 12.7, 23.0, 28.6, 32.2, 34.4, 34.9, 42.7, 56.6, 57.0, 59.1, 66.7, 72.3, 81.3, 81.5, 81.7, 109.2, 111.7, 126.6, 126.8, 132.6, 134.0, 135.0, 135.6, 140.4, 146.3, 156.2, 168.4, 178.7, 186.1. Electrospray ionization time-of-flight mass spectrometry ("ESI TOF MS") m/z 633.3507, calculated for $C_{32}H_{49}N_4O_9$ ([M+H]$^+$) 633.3494.

EXAMPLE 2

Compounds I in which $Q^1$ is a quaternary nitrogen group (or compounds III) can be synthesized either by the reaction of a corresponding geldanamycin compound with a suitable amine bearing a quaternary nitrogen group, as shown by procedure of Scheme 2a using (2-aminoethyl)trimethylammonium chloride as the exemplar or by reaction of a suitable diamine having a tertiary nitrogen group followed by alkylation with an alkylating agent $R^1X$, as shown by the procedure of Scheme 2b using (2-dimethylamino)ethylamine as an exemplar. Exemplary suitable alkylating agents $R^1X$ include methyl iodide, allyl bromide, bromoacetonitrile, and 2-bromoacetamide.

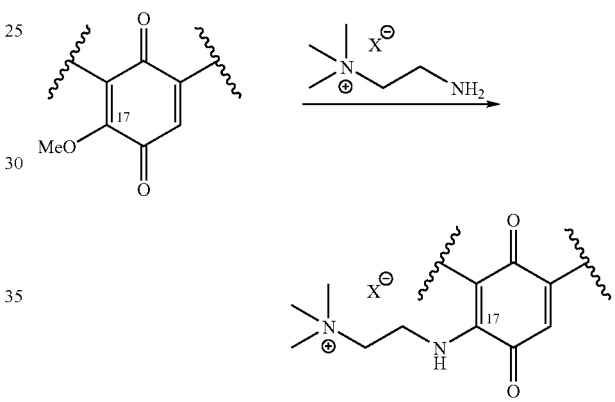

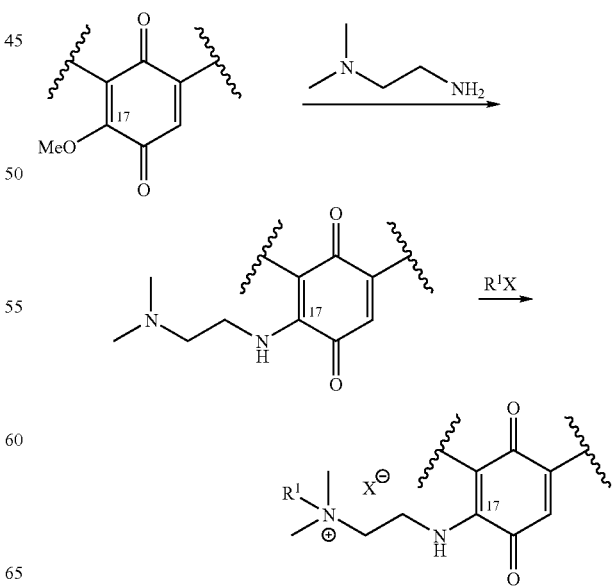

The following detailed procedure (per Scheme 2a) used to synthesize compound 3 ({[2-(17-demethoxygeldanamycin-17-yl)amino]ethyl}trimethylammonium chloride) is representative.

To a solution of geldanamycin (56 mg, 0.1 mmol) in dimethylsulfoxide ("DMSO," 4 mL) at 60° C. was added (2-aminoethyl)trimethylammonium chloride hydrochloride (0.2 mmol). (The primary amine was released using triethylamine.) The mixture was stirred 60° C. until the geldanamycin was fully consumed as indicated by TLC. The crude product was purified either by flash chromatography or by reversed-phase HPLC, giving compound 3 as a purple solid. ESI TOF MS m/z 631.3702, calculated for $C_{33}H_{51}N_4O_8$ ($M^+$) 631.3702.

EXAMPLE 3

Compounds I in which $Q^1$ is a sulfonic acid group (or compounds IV) can be synthesized by the reaction of a corresponding geldanamycin compound with a suitable aminosulfonic acid, as shown by procedure of Scheme 3 using 3-amino-1-propanesulfonic acid as an exemplar. The reaction can be performed in DMSO in the presence of a base such as triethylamine.

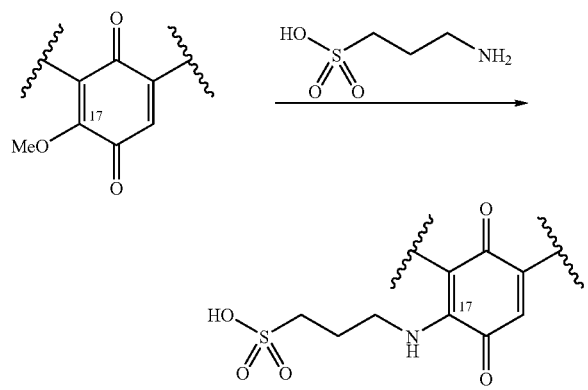

Scheme 3

The corresponding sulfonic acid compound derived from 2-amino-1-ethanesulfonic acid is disclosed in Schnur et al., *J. Med. Chem.* 38 (19), 3806-3812 (1995), the disclosure of which is incorporated herein by reference.

EXAMPLE 4

Compounds I in which $Q^1$ is a phosphonic acid group (or compounds V) were synthesized by the reaction of a corresponding geldanamycin compound with a suitable aminophosphonic acid, as shown by procedure of Scheme 4 using 2-aminoethylphosphonic acid as an exemplar. The reaction was performed a suitable solvent as noted below, in the presence of a base such as triethylamine to release the primary amine. A typical scale was 0.1 mmol (56 mg) geldananycin and 0.2 mmol aminophosphonic acid. The reaction mixture was stirred at 20 to 60° C. until the starting geldanamycin was fully consumed, as indicated by thin layer chromatography. The crude product was purified by either flash chromatography or by reversed phase HPLC, giving the product as a purple solid.

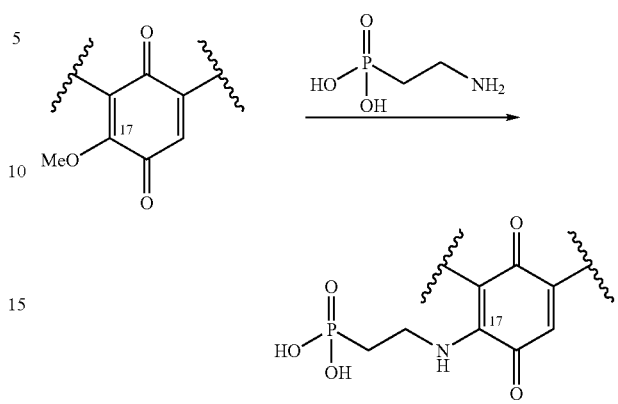

Scheme 4

Compound 8 was synthesized following the above general synthetic method using 2-aminoethylphosphonic acid in 12:12:1 (v/v) dichloroethane/methanol/water mixture at 60° C. $^{13}C$ NMR (CD$_3$OD, 100 MHz) δ (relative to CD$_3$OD at 49.0 ppm) 12.4, 13.5, 14.1, 22.6, 30.2 (d, $^1J_{C-P}$=131 Hz), 31.2, 33.8, 34.3, 35.6, 42.9, 56.8, 57.5, 74.3, 82.1 (2C), 83.0, 109.2, 109.5, 127.2, 129.5, 132.9, 134.4, 135.4, 137.8, 142.9, 146.9, 159.1, 170.7, 180.8, 185.9. ESI TOF MS m/z 652.2627, calcd for $C_{30}H_{43}N_3O_{11}P$ ([M–H]$^-$) 652.2641.

Compound 9 was synthesized following the general synthetic method above using 3-aminopropylphosphonic acid in 8:8:1 (v/v) dichloroethane/methanol/water mixture at 60° C. ESI TOF MS m/z 690.2780, calcd for $C_{31}H_{46}N_3O_{11}NaP$ ([M+Na]$^+$) 690.2762.

Compound 10 was synthesized following the general synthetic method above using 4-aminobutylphosphonic acid (the primary amine was released using triethylamine) in 8:8:1 (v/v) dichloroethane/methanol/water mixture at 60° C. ESI TOF MS m/z 704.2948, calcd for $C_{32}H_{48}N_3O_{11}NaP$ ([M+Na]$^+$) 704.2919.

EXAMPLE 5

Compounds I in which $Q^1$ is a glycoside group can be synthesized by the reaction of a corresponding geldanamycin compound with a suitable aminoglycoside, as shown by procedure of Scheme 5.

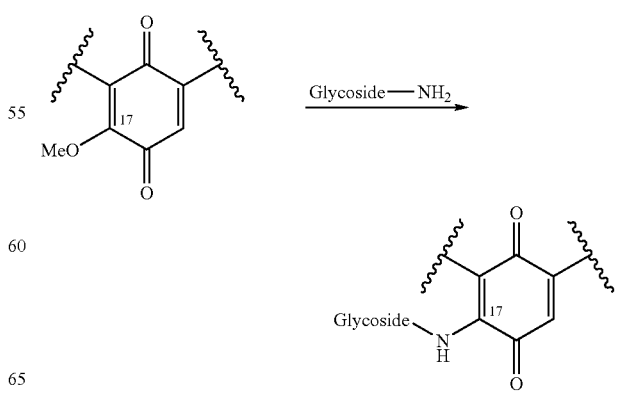

Scheme 5

The following procedures for the synthesis of compounds 1 (17-(glucos-2-amino)-17-demethoxygeldanamycin) and 2 (17-(glucos-6-amino)-17-demethoxygeldanamycin) are illustrative.

Compound 1. To a solution of geldanamycin (56 mg, 0.1 mmol) in DMSO (4 mL) at 50° C. was added glucosamine hydrochloride (0.2 mmol). (The primary amine was released using triethylamine.) The mixture was stirred at 50° C. until the geldanamycin was fully consumed as indicated by TLC. The crude product was purified either by flash chromatography or by reversed-phase HPLC, giving compound 1 as a purple solid. $^{13}$C NMR (CD$_3$OD, 100 MHz) δ (relative to CD$_3$OD at 49.0 ppm) 12.4, 13.6, 14.4, 22.6, 31.5, 33.7, 34.6, 36.0, 56.9, 57.5, 62.6, 71.9, 73.3, 74.0, 74.9, 81.8, 81.8, 81.8, 82.7, 92.8, 109.4, 110.9, 127.1, 129.6, 132.4, 134.5, 135.4, 137.7, 142.4, 147.5, 159.0, 170.7, 181.3, 185.8. ESI TOF MS m/z 730.3204, calculated for C$_{34}$H$_{49}$N$_3$O$_{13}$ ([M+Na]$^+$) 730.3158.

Compound 2. To a solution of geldanamycin (56 mg, 0.1 mmol) in DMSO (4 mL) at 20° C. was added 6-amino-6-deoxy-(D)-glucose hydrochloride (0.2 mmol). (The primary amine was released using triethylamine.) The mixture was stirred at 20° C. until the geldanamycin was fully consumed as indicated by TLC. The crude product was purified either by flash chromatography or by reversed-phase HPLC, giving compound 2 as a purple solid. $^{13}$C NMR (CD$_3$OD, 100 MHz) δ (relative to CD$_3$OD at 49.0 ppm) 12.4, 13.6, 14.3, 22.7, 31.5, 33.6, 34.5, 35.7, 56.8, 57.5, 70.7 (2C), 73.4, 73.8 (2C), 74.3 (2C), 74.6, 75.4, 76.2, 77.7, 82.0 (2C), 83.0, 94.1, 98.4, 109.1, 110.0, 127.1, 129.6, 132.6, 134.4, 135.3, 138.0, 142.7, 146.7, 159.1, 170.6, 181.2, 185.6. ESI TOF MS m/z 730.3156, calculated for C$_{34}$H$_{49}$N$_3$O$_{13}$Na ([M+Na]$^+$) 730.3158.

EXAMPLE 6

Compounds I in which Q$^1$ is a biotinyl group can be synthesized by the reaction of a corresponding geldanamycin compound with a suitable biotinylated amine, as shown by procedure of Scheme 6.

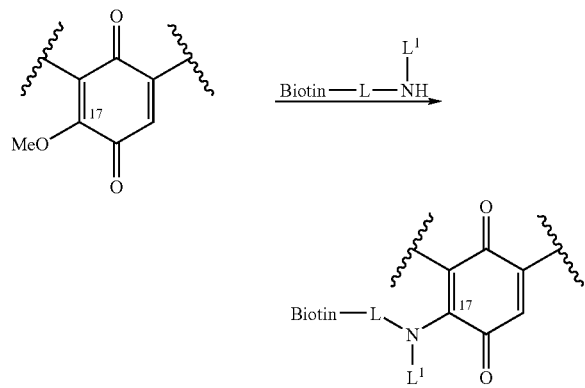

The following syntheses of compounds 5 and 6 are illustrative.

Compound 5. To a solution of geldanamycin (56 mg, 0.1 mmol) in methanol (4 mL) at 20° C. was added Biotin-PEO-amine (Pierce, Rockford, Ill.; 0.2 mmol). The mixture was stirred at 20° C. until the geldanamycin was fully consumed as indicated by TLC. The crude product was purified either by flash chromatography or by reversed-phase HPLC, giving compound 5 as a purple solid. $^{13}$C NMR(CDCl$_3$, 100 MHz) δ (relative to CDCl$_3$ at 77.0 ppm) 12.4, 12.6, 12.8, 23.0, 25.5, 28.0, 28.1, 29.7, 32.3, 34.2, 34.8, 35.9, 39.2, 40.5, 45.2, 55.3, 56.7, 57.2, 60.1, 61.7, 68.6, 70.0, 70.2, 70.4, 72.6, 81.3, 81.4, 81.6, 108.5, 108.8, 126.4, 127.2, 132.8, 133.5, 134.7, 136.2, 141.5, 145.0, 156.3, 163.6, 168.5, 173.4, 180.5, 184.2. ESI TOF MS m/z 903.4555, calculated for C$_{44}$H$_{67}$N$_6$O$_{12}$S ([M+H]$^+$) 903.4532.

Compound 6. To a solution of geldanamycin (56 mg, 0.1 mmol) in methanol (4 mL) at 20° C. was added Biotin-PEO-LC-amine (Pierce, Rockford, Ill.; 0.2 mmol). The mixture was stirred at 20° C. until the geldanamycin was fully consumed as indicated by TLC. The crude product was purified either by flash chromatography or by reversed-phase HPLC, giving compound 6 as a purple solid. ESI TOF MS m/z 947.4799, calculated for C$_{46}$H$_{71}$N$_6$O$_{12}$S ([M+H]$^+$) 947.4794.

EXAMPLE 7

Compounds I in which Q$^1$ is a carboxylic acid or zwitterionic group (or compounds VI) can be synthesized by the reaction of a corresponding geldanamycin compound with a suitable amino acid, as shown by procedure of Scheme 7 using β-alanine as an exemplar.

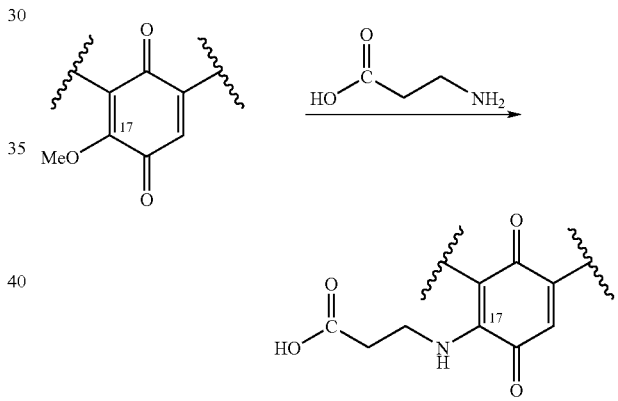

A procedure for preparing 17-β-alanyl-17-demethoxygeldanamycin is disclosed in Schnur et al., U.S. Pat. No. 5,932,566 (1999), the disclosure of which is incorporated herein by reference.

EXAMPLE 8

The human breast cancer cell line SKBr3 was obtained from the American Type Culture Collection (Manassas, Va.) and maintained in McCoy's 5A modified medium (Invitrogen; Carlsbad, Calif.) supplemented with 10% fetal bovine serum (FBS) (Hyclone; Logan, Utah) and 2 mM glutamine, in humidified air with 5% CO$_2$ at 37° C.

Cells were seeded in duplicate in 96-well black tissue culture microtiter plates at ~4000 cells per well and allowed to attach overnight. Serial 10-fold dilutions of compounds were added, and the cells were incubated for 72 h. Cell viability was determined using the CellTiter-Glo™ Luminescent Cell Viability Assay (Promega; Madison, Wis.). IC$_{50}$ is defined as the concentration of drug required for inhibiting cell growth by 50%.

Truncated (Carreras et al. *Anal. Biochem.* 2003, 317, 40-46) and full-length forms of human Hsp90 were expressed in *E. coli* with N-terminal polyHis and biotinylation recognition sequence (BRS) tags to facilitate purification and SPA assay, respectively. The tagged full length Hsp90 sequence consisted of the natural Hsp90α (Hickey et al., *Mol. Cell Biol.* 1989, 9, 2615-2626) sequence preceded by the sequence MSH$_{10}$SLTDIFEAOKIEWHHMA where the BRS is underlined. The 3' end of the gene contained a BamHI site, adding a single proline residue to the C-terminus. The tagged full-length protein was cloned into pET21d as described for the tagged N-domain of Hsp90 (Carreras et al., cited supra), and co-expressed with biotin ligase encoded by pBIRAcm (Avidity, Denver, Colo.) in *Escherichia coli* BL21DE(3).

Biotinylated Hsp90α was added to a 1 mg/mL suspension of streptavidin coated YiSi beads (Pharmacia RPNQ0012; 219 pmol streptavidin/mg) in Binding Buffer (10 mM Tris-HCl, 5 mM MgCl$_2$, pH 7.0) to obtain a final concentration of 225 nM. [allyl-$^3$H]-17-AAG (2000 cpm/pmol) was then added to a final concentration of 2 μM, and 50 μL aliquots of the resulting suspension were mixed with 50 μL aliquots of 0.1 to 50 μM test compounds in Binding Buffer. Reaction mixtures were incubated for 2~4 h at room temperature in 96-well assay plates, then signals for each reaction were measured using a Wallac Microbeta scintillation counter. The resulting data was fit to a competitive binding equation (Segal, I. H., *Enzyme Kinetics: Behavior and analysis of rapid equilibrium and steady-state enzyme systems*; Wiley Interscience: New York, 1975).

The results are presented in Table A.

TABLE A

| Compound | Cytotoxicity, SKBr3 Cells (IC$_{50}$ (nM)) | Hsp90α Binding (K$_d$ (μM)) |
| --- | --- | --- |
| 1 | 1,200 | 0.5 |
| 2 | 5,300 | 0.2 |
| 3 | >1,000 | 0.3 |
| 4 | >1,000 | 0.6 |
| 5 | >1,000 | 1.3 |
| 6 | >1,000 | 1.1 |
| 7 | >5,000 | 1.1 |
| 8 | ~3,000 | 0.6 |
| 9 | ~1,000 | 0.9 |
| 10 | ~2,000 | 1.3 |
| 17-AAG (comparative) | 38 | 1.3 |

The above results show that compounds of this invention have markedly lower cytotoxicities compared to the clinical candidate 17-AAG, indicative of an inability to pass through a cell membrane and enter cells. However, they retain an ability to bind strongly to Hsp90, thereby inhibiting it.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

What is claimed is:

1. A compound having a structure according to formula III

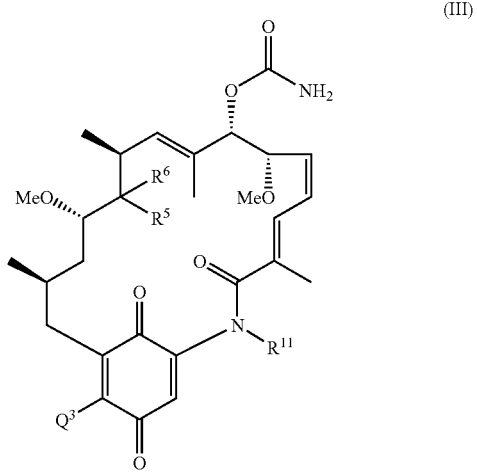

(III)

or a pharmaceutically acceptable salt thereof, wherein
    Q$^3$ is selected from the group consisting of

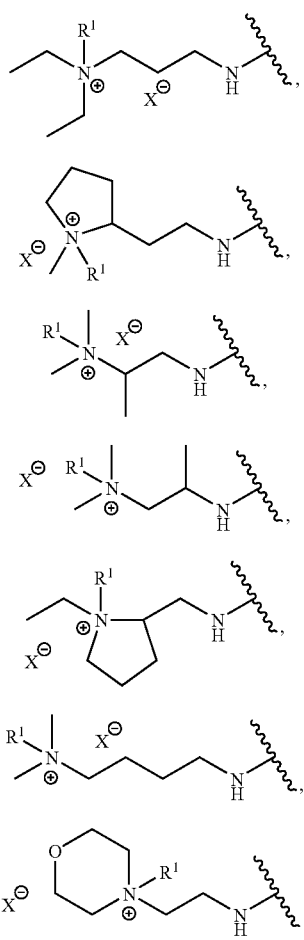

-continued

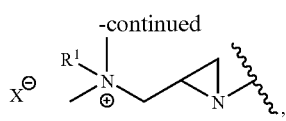

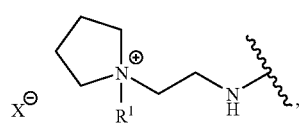

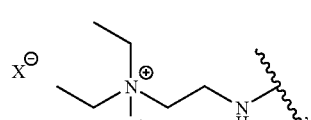

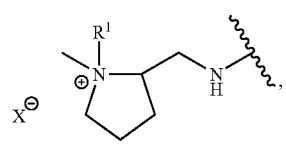

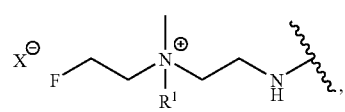

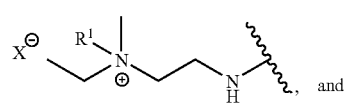

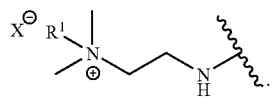

$R^1$ is $C_1$-$C_5$ alkyl, $C_1$-$C_5$ alkenyl, $C_1$-$C_5$ alkynyl, $CH_2CN$, or $CH_2CONH_2$;
$R^5$ is H, $OR^8$, halogen, $OC(=O)R^8$, $O(C=O)N(R^8R^9)$, $OSO_2R^{10}$, or $O(C=O)NHSO_2N(R^8R^9)$;
$R^6$ is H or halogen; or $R^5$ and $R^6$ combine to form =O or =$NOR^8$;
each $R^8$ is independently H, $C_1$-$C_5$ alkyl, $C_2$-$C_5$ alkenyl, $C_2$-$C_5$ alkynyl, or $C_3$-$C_6$ cycloalkyl;
each $R^9$ is independently H, $C_1$-$C_5$ alkyl, $C_2$-$C_5$ alkenyl, $C_2$-$C_5$ alkynyl, or $C_3$-$C_6$ cycloalkyl;
$R^8$ and $R^9$ form, in combination with a nitrogen atom to which they are commonly attached, a 3, 4, 5, or 6 membered heterocyclic ring, which is an aziridinyl, azetidinyl, pyrrolidinyl. or piperidinyl ring;
$R^{10}$ is $C_1$-$C_5$ alkyl, $C_2$-$C_5$ alkenyl, $C_2$-$C_5$ alkynyl, or $C_3$-$C_6$ cycloalkyl;
$R^{11}$ is H, $C_1$-$C_5$ alkyl, $C_2$-$C_5$ alkenyl, $C_2$-$C_5$ alkynyl; and
$X^\ominus$ is a pharmaceutically acceptable counteranion.

2. A compound according to claim 1, wherein $R^5$ is OH and $R^6$ and $R^{11}$ are each H.

3. A compound according to claim 1, having a structure according to formula 3

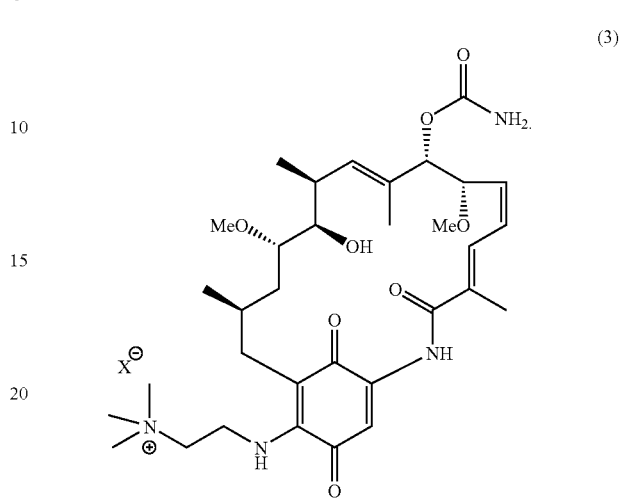

(3)

4. A pharmaceutical composition comprising a compound according to claim 1 and an excipient.

5. A compound having a structure according to formula IV

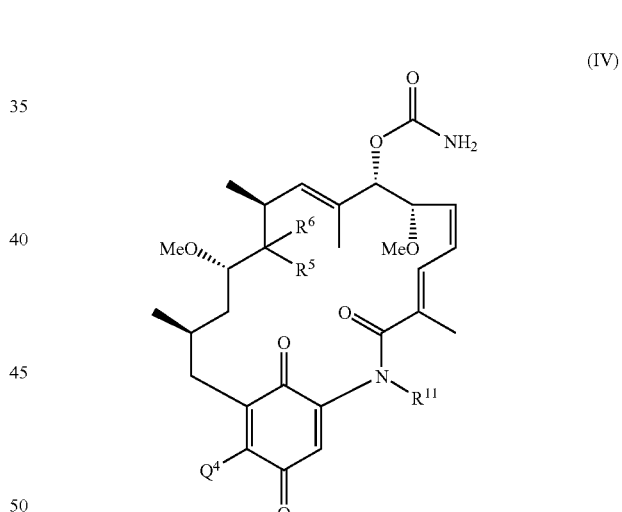

(IV)

or a pharmaceutically acceptable salt thereof, wherein
$Q^4$ is selected from the group consisting of

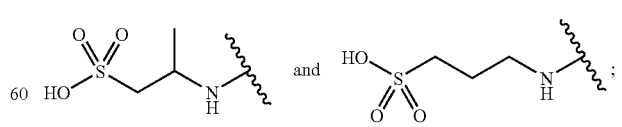

$R^5$ H, $OR^8$, halogen, $OC(=O)R^8$, $O(C=O)N(R^8R^9)$, $OSO_2R^{10}$, or $O(C=O)NHSO_2N(R^8R^9)$;
$R^6$ is H or halogen; or $R^5$ and $R^6$ combine to form =O or =$NOR^8$;

each $R^8$ is independently H, $C_1$-$C_5$ alkyl, $C_2$-$C_5$ alkenyl, $C_2$-$C_5$ alkynyl, or $C_3$-$C_6$ cycloalkyl;

each $R^9$ is independently H, $C_1$-$C_5$ alkyl, $C_2$-$C_5$ alkenyl, $C_2$-$C_5$ alkynyl, or $C_3$-$C_6$ cycloalkyl;

$R^8$ and $R^9$ form, in combination with a nitrogen atom to which they are commonly attached, a 3, 4, 5, or 6 membered heterocyclic ring, which is an aziridinyl, azetidinyl, pyrrolidinyl, or piperidinyl ring;

$R^{10}$ is $C_1$-$C_5$ alkyl, $C_2$-$C_5$ alkenyl, $C_2$-$C_5$ alkynyl, or $C_3$-$C_6$ cycloalkyl; and $R^{11}$ is H, $C_1$-$C_5$ alkyl, $C_2$-$C_5$ alkenyl, $C_2$-$C_5$ alkynyl.

6. A compound according to claim 5, wherein $R^5$ is OH and $R^6$ and $R^{11}$ are each H.

7. A pharmaceutical composition comprising a compound according to claim 5 and an excipient.

8. A compound having a structure according to formula V (V)

[Structure of formula V]

or a pharmaceutically acceptable salt thereof. wherein $Q^5$ is selected from the group consisting of

[Structures]

, and

-continued

[Structure]

;

$R^5$ H, $OR^8$, halogen, $OC(=O)R^8$, $O(C=O)N(R^8R^9)$, $OSO_2R^{10}$, or $O(C=O)NHSO_2N(R^8R^9$ $R^6$ is H or halogen; or $R^5$ and $R^6$ combine to form =O or =NOR$^8$;

each $R^8$ is independently H, $C_1$-$C_5$ alkyl, $C_2$-$C_5$ alkenyl, $C_2$-$C_5$ alkynyl, or $C_3$-$C_6$ cycloalkyl;

each $R^9$ is independently H, $C_1$-$C_5$ alkyl, $C_2$-$C_5$ alkenyl, $C_2$-$C_5$ alkynyl, or $C_3$-$C_6$ cycloalkyl; or $R^8$ and $R^9$ form, in combination with a nitrogen atom to which they are commonly attached, a 3, 4, 5, or 6 membered heterocyclic ring, which is an aziridinyl, azetidinyl, pyrrolidinyl, or piperidinyl ring;

$R^{10}$ is $C_1$-$C_5$ alkyl, $C_2$-$C_5$ alkenyl, $C_2$-$C_5$ alkynyl, or $C_3$-$C_6$ cycloalkyl; and $R^{11}$ is H, $C_1$-$C_5$ alkyl, $C_2$-$C_5$ alkenyl, $C_2$-$C_5$ alkynyl.

9. A compound according to claim 8, wherein $R^5$ is OH and $R^6$ and $R^{11}$ are each H.

10. A compound according to claim 8, having a structure according to formula 8, 9, or 10:

(8)

[Structure]

(9)

[Structure]

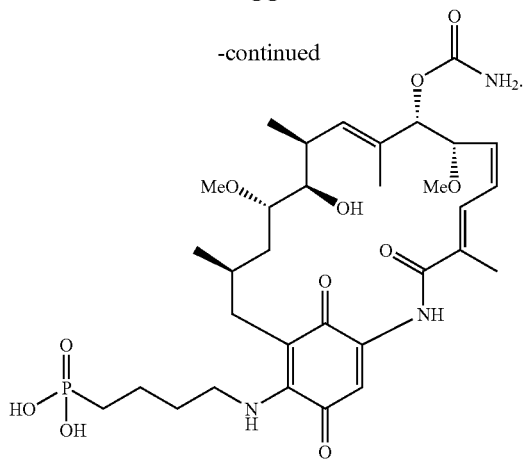

11. A pharmaceutical composition comprising a compound according to claim 8 and an excipient.

12. A compound having a structure according to formula VI

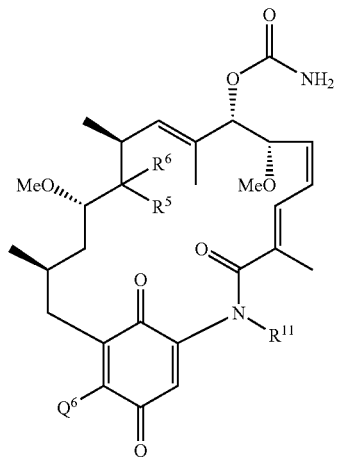

(VI)

or a pharmaceutically acceptable salt thereof, wherein $Q^6$ is selected from the group consisting of

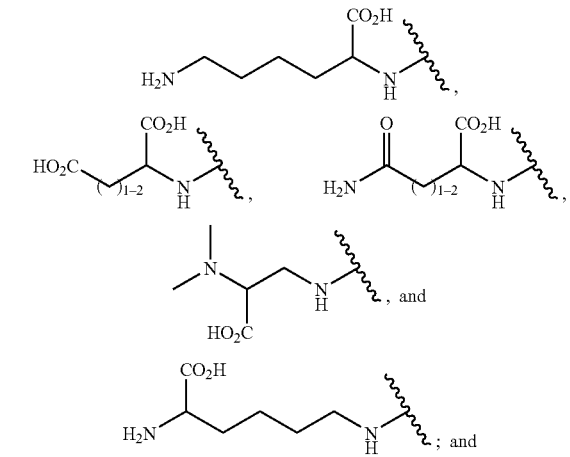

$R^5$ is H, $OR^8$, halogen, $OC(=O)R^8$, $O(C=O)N(R^8R^9)$, $OSO_2R^{10}$, or $O(C=O)NHSO_2N(R^8R^9)$;

$R^6$ is H or halogen; or $R^5$ and $R^6$ combine to form $=O$ or $=NOR^8$;

each $R^8$ is independently H, $C_1$-$C_5$ alkyl, $C_2$-$C_5$ alkenyl, $C_2$-$C_5$ alkynyl, or $C_3$-$C_6$ cycloalkyl;

each $R^9$ is independently H, $C_1$-$C_5$ alkyl, $C_2$-$C_5$ alkenyl, $C_2$-$C_5$ alkynyl, or $C_3$-$C_6$ cycloalkyl;

$R^8$ and $R^9$ form, in combination with a nitrogen atom to which they are commonly attached, a 3, 4, 5, or 6 membered heterocyclic ring, which is an aziridinyl, azetidinyl, pyrrolidinyl, or piperidinyl ring;

$R^{10}$ is $C_1$-$C_5$ alkyl, $C2$-$C_5$ alkenyl, $C_2$-$C_5$ alkynyl, or $C_3$-$C_6$ cycloalkyl; and $R^{11}$ is H, $C_1$-$C_5$ alkyl, $C_2$-$C_5$ alkenyl, $C2$-$C_5$ alkynyl.

13. A pharmaceutical composition comprising a compound according to claim 12 and an excipient.

\* \* \* \* \*